United States Patent [19]

Beggs et al.

[11] Patent Number: 4,495,957

[45] Date of Patent: Jan. 29, 1985

[54] FLOSSING DEVICE

[76] Inventors: George Beggs, 1740 Spruce La.; Thomas H. Richardson, 610 Southerncross Dr., both of Colorado Springs, Colo. 80906

[21] Appl. No.: 439,537

[22] Filed: Nov. 5, 1982

[51] Int. Cl.³ .............................................. A61C 15/00
[52] U.S. Cl. ................................................. 132/92 A
[58] Field of Search .................... 132/89, 90, 91, 92 R, 132/92 A; 242/137.1, 138, 146

[56] References Cited

U.S. PATENT DOCUMENTS

| | | | |
|---|---|---|---|
| 2,644,469 | 7/1953 | Cohen | 132/92 R |
| 3,378,017 | 4/1968 | Stiles | 132/92 R |
| 3,871,393 | 3/1975 | Wharton | 132/92 R |
| 3,882,879 | 5/1975 | Lucas | 132/92 R |

Primary Examiner—Richard J. Apley
Assistant Examiner—Carolyn A. Harrison
Attorney, Agent, or Firm—Hubbell, Cohen, Stiefel & Gross

[57] ABSTRACT

A flossing device (10) having a body (12) comprising a handle portion (26) and a barrel portion (28) terminating in a pair of spaced prongs (16, 18). A spool of floss (24) is mounted on the body (12), and is threaded about the body (12) in a plurality of grooves (70, 72, 74, 76) such that a length of floss (80) for flossing the teeth extends across the space between the prongs (16, 18). A trigger mechanism (20) operable by the same hand used to grasp the device (10) pinches the floss for tensioning the length (80) in one position and releases the floss for advancement to expose a new, clean length of floss (80) in a second position. The trigger mechanism (20) is moveable to a position wherein all soiled surfaces are fully exposed for cleaning.

21 Claims, 6 Drawing Figures

1

FLOSSING DEVICE

TECHNICAL FIELD

This invention pertains to tooth care implements and more particularly to flossing devices.

BACKGROUND ART

Devices to aid in the flossing of teeth are well known. Despite the large number of patents disclosing such devices, they have met with little commercial success, and the primary flossing technique still consists of tensioning a length of floss between the user's hands. An acceptable flossing device must possess a number of attributes, some of the more important being ease of use, ability to thoroughly clean the device, ease of construction, and modest cost. All of the prior art devices known to applicants are deficient in one or more of the foregoing respects, and it is perhaps for this reason that they have not achieved commercial success.

The prior art discloses many flossing devices wherein a spool of floss is supported on the device, the free end of the floss being tensioned across a pair of prongs at one end of the device, the prongs being spaced such that the length of floss therebetween may be inserted between the teeth for effecting cleaning.

A principal drawback of one such device disclosed in U.S. Pat. No. 3,886,956, is the requirement that tension be effected by having the user pull on the free end of the floss during cleaning. Inasmuch as the user must grasp the device with one hand, tensioning must be effected with the other hand, and this device therefore offers little or no advantage over the usual technique of simply stretching the length of floss between the hands.

In other prior art flossing devices of the type of interest here, the floss is tensioned by securing the free end in some fashion to the body of the device. While these flossing devices are advantageous in that the flossing operation may be accomplished with one hand, the known devices have a variety of drawbacks. For example, in U.S. Pat. No. 3,939,853, a button is secured to the device behind the prongs, and tensioning is effected by wrapping the floss about the small space between the button and the body of the device. However, inasmuch as it is necessary to advance a clean length of floss into the space between the prongs after one or at most a few cleaning operations, this arrangement is disadvantageous as the technique for advancing the floss, comprising unwinding the floss from around the button, pulling on the floss, and then rewinding the floss on the button, is cumbersome and time consuming.

A similar drawback is evident in still other flossing devices of the type of interest here. Thus, in the devices disclosed in U.S. Pat. Nos. 2,837,098 and 3,814,114, tensioning of the floss is effected by an axially moveable or rotatable member which traps the free end of the floss, and also the length of floss extending from the spool to the prongs, in a passage formed in the body of the device. In these devices, advancement of the floss for exposing a clean length of floss between the prongs requires grasping the device with one hand, moving the tensioning means, pulling on the floss to advance it, and then again moving the tensioning means to retension the floss. Inasmuch as the tensioning means in these devices cannot be manipulated by the same hand being used to hold the flossing device, it will be apparent that floss advancement is cumbersome and requires a certain amount of dexterity.

In the devices disclosed in FIGS. 4-6 of U.S. Pat. No. 3,924,647, the free end of the floss passes through a hole in the body and is tensioned by a plug or the like disposed in the hole and moveable between a position wherein the floss is trapped between the plug and the defining walls of the passage, and another position wherein the strand is freed for pulling on the free end thereof for advancing the floss. Because the free end of the floss comprises floss which has been previously used in a cleaning operation and is thereby soiled, the passage through which the free end passes also eventually becomes soiled. As this passage extends through the device, it will be apparent that cleaning of the passage is quite difficult, unless a specially shaped implement designed to fit in the passage is used. This is also true of the devices mentioned in U.S. Pat. Nos. 2,837,098 and 3,814,114 discussed above.

U.S. Pat. No. 3,847,168 discloses a device similar to that disclosed in U.S. Pat. No. 3,886,956, excepting that the free end of the floss does not pass through the same passage as the plug, but rather is trapped between an enlarged head of the plug and the confronting surface of the body of the flossing device. Again, however, it will be apparent that the space between the enlarged plug head and the body of the device will inevitably become soiled, and because the clearance in this space is quite small, thorough cleaning of this device is also difficult. In addition, in this device the free end of the floss is not inherently retained in position under the enlarged head of the plug when the plug is moved to the position wherein the floss is freed for advancement. Consequently, this device also suffers the drawback of cumbersome operation as the user is required to manually position the floss under the plug head after each advancement.

It is therefore an object of the present invention to provide a flossing device which requires a minimal amount of dexterity to use, and which may be readily and easily cleaned.

It is a further object of the present invention to provide a flossing device wherein the body of the device is shaped to maximize the efficiency and simplicity of the flossing operation.

DISCLOSURE OF THE INVENTION

In accordance with the present invention, we have developed a flossing device comprising a body having a handle portion dimensioned for grasping by one hand of the user, and a barrel portion extending from one end of the handle portion, the free end of the barrel comprising a pair of prongs defining a space therebetween at their free ends. Means are provided for securing a spool of floss to the body for rotation relative thereto, and the body is provided with grooves defining a path for the floss about the body from the securing means, over a surface portion of the body, across the space between the prongs and back over the body surface portion.

The device further includes a trigger member, and means for securing the trigger member to the body for movement by the same hand used to grasp the device between one position wherein a surface of the trigger contacts the surface portion of the body for securing both lengths of floss passing thereover against movement for tensioning the floss extending across the space between the prongs, and a second position wherein the trigger surface is spaced from the body surface portion for accommodating advancement of the floss along the path by pulling on the free floss end with the other hand for moving a clean length of floss into the space between the prongs. The device also includes means operable by the hand grasping the device for releasably securing the trigger member in the one position.

As the floss is being advanced while the trigger is in the second position, the grooves serve to retain the floss in the floss path whereby the device is rereadied for use by simply moving the trigger back to the one position. The trigger is also moveable to a third position wherein the trigger surface and the body surface portion are sufficiently spaced to expose both surfaces for cleaning.

Further features and advantages of the flossing device in accordance with the present invention will be more fully apparent from the following detailed description and annexed drawings of the presently preferred embodiment thereof.

BRIEF DESCRIPTION OF THE DRAWINGS

In the drawings, wherein like numerals represent like parts.

BEST MODE FOR CARRYING OUT THE INVENTION

Figure 1:
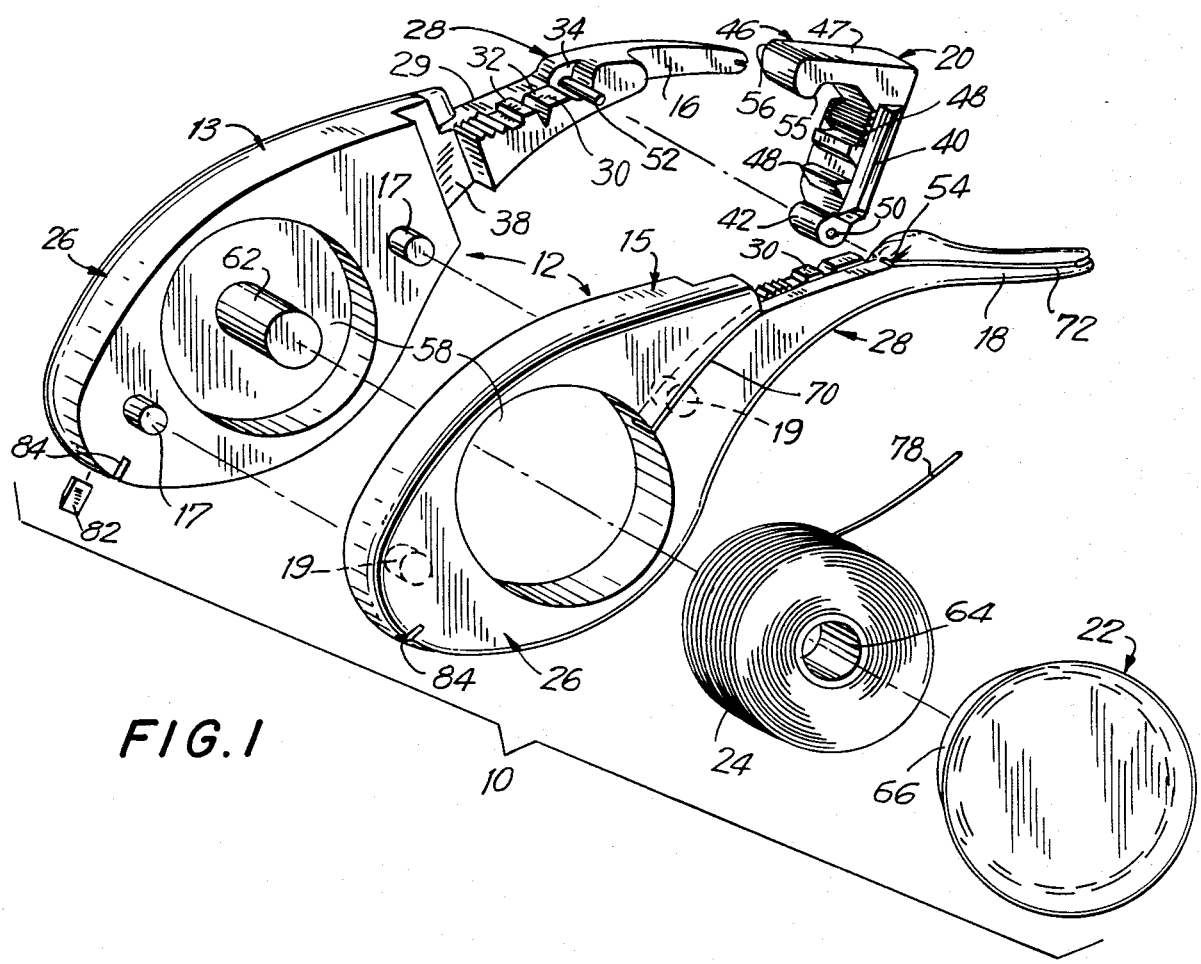
FIG. 1 is an exploded perspective view of the preferred embodiment of the flossing device in accordance with the present invention.
Figure 2:
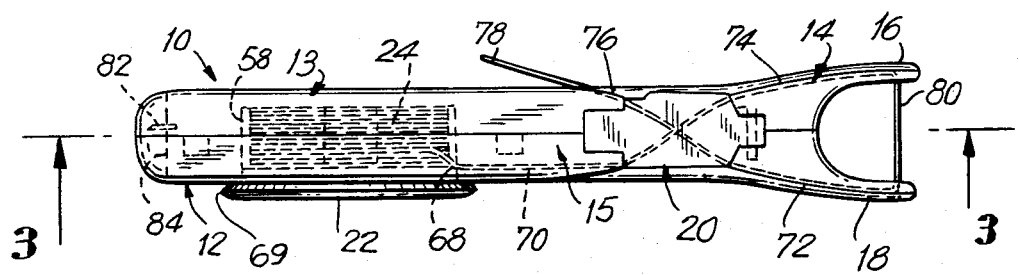
FIG. 2 is a top plan view thereof.
Figure 3:
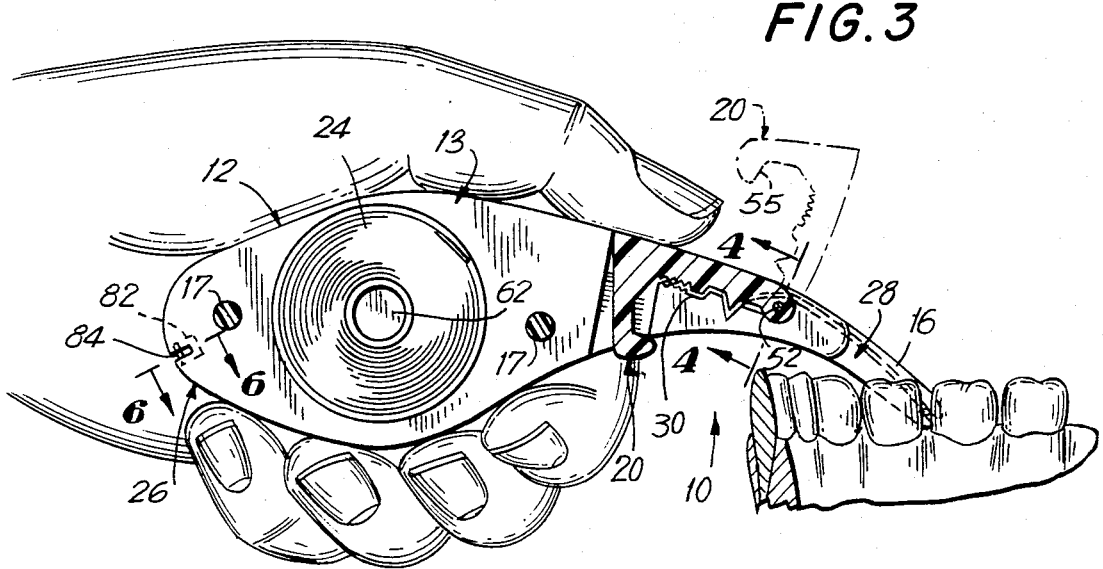
FIG. 3 is a sectional view taken substantially along the line 3—3 in FIG. 2 and showing the manner of use of the preferred flossing device of the present invention.
Figure 4:
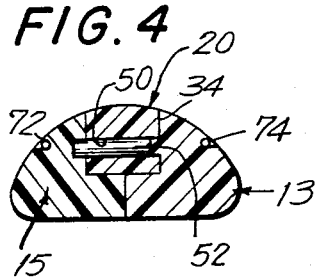
FIG. 4 is a sectional view taken substantially along the line 4—4 in FIG. 3.
Figure 5:
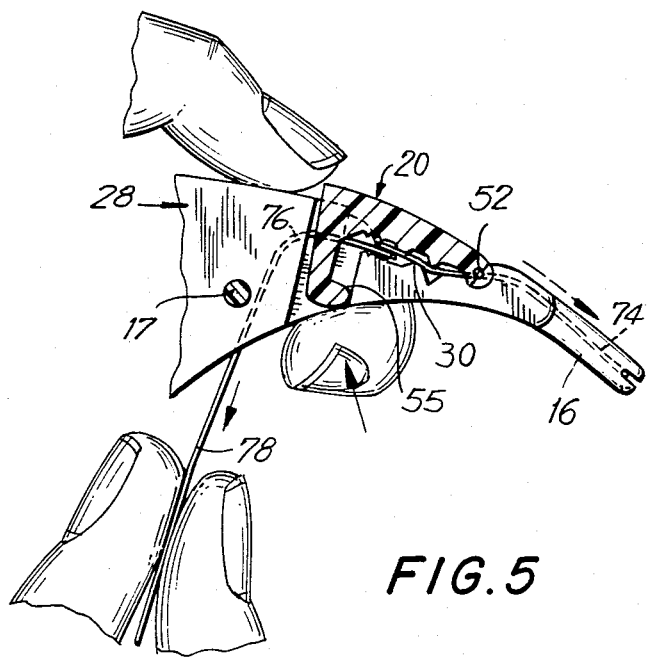
FIG. 5 is a fragmentary sectional view similar to FIG. 3 but showing the trigger mechanism in the floss advancing position.

Referring now to the drawings, and initially to FIGS. 1-3 thereof, the preferred flossing device in accordance with the present invention is generally designated by the reference numeral 10. As shown, the device 10 includes a generally gun-shaped body 12, a trigger mechanism 20, and a cap 22.

The skilled art worker will recognize that the body 12 may be formed in a variety of ways and from a variety of different materials. We presently prefer to form the body 12 in separate halves 13, 15 joined along the longitudinal axis of the body 12. The separate halves 13, 15 are preferably injection molded from plastic, such as polycarbonate ABS, and are joined together by integral projections 17 on one half 13 which snap fit into corresponding holes 19 formed in the other half 15 (FIG. 1), only some of the contemplated projections 17 and holes 19 being shown in FIG. 1. As the details of such construction are well within the capabilities of the skilled art worker, a further description is unnecessary. To reduce material costs, the body halves 13, 15 may be hollowed out, this not being shown in the drawings. Trigger mechanism 20 and cap 22 are also preferably injection molded from plastic, such as polycarbonate ABS.

As is apparent from FIGS. 1-3, the generally gun-shaped body 12 includes an enlarged portion 26 which defines a handle for holding the device 10 during use, and a barrel portion 28 which extends forwardly and downwardly in an arcuate fashion relative to the handle 26, the barrel portion having a generally U-shaped forward end 14 defining a pair of prongs or tines 16, 18. As will be more fully apparent hereinafter, the arcuate shape of the barrel portion 28 serves to facilitate use of the device 10.

Referring now to FIGS. 1-5, the upper surface of the barrel portion 28 between the forward end 14 and handle portion 26 is formed with a generally rectangular recess 29 defining a surface 30. As shown, a pair of transverse indents 32 are formed in the surface 30, the indents 32 preferably being closed at either end by the defining walls of the body 12. A centrally disposed blind slot 34 is formed in the body 12 for communication with the recess 29 at the forward end thereof, the lower defining wall 36 of the slot 34 extending beneath the surface 30. A through passage 38 is formed in the body 12 at the other end of the recess 29, the passage 38 extending between the upper and lower surfaces of the body 12, the upper portion of the passage 38 communicating with the recess 29. As shown, the passage 38 is preferably of generally rectangular cross-section.

As is apparent from the drawings, the trigger mechanism 20 is dimensioned to be received in the recess 29. Thus, trigger mechanism 20 includes a main portion 40, a generally cylindrical member 42 depending from one end of the portion 40 and dimensioned for seating in the slot 34, an elongate generally L-shaped member 46 depending from the other end of the portion 40 and dimensioned for disposition in the passage 38, and a pair of intermediate transverse ridges 48 dimensioned for seating in the grooves 32 in the surface 30 of the recess 29. The member 42 of the trigger mechanism 20 is provided with a transverse hole 50. The hole 50 is dimensioned to receive with clearance a projection 52 extending from one defining side wall of the slot 34 and integrally formed with one half 13 of the body 12. The free end of projection 52 is dimensioned for a snap fit in a blind hole 54 formed in the other defining wall of the slot 34 in the other body half 15.

As best shown in FIG. 1, assembly of the body 12 and trigger mechanism 20 is accomplished by passing the projection 52 through the hole 50, and then securing the two halves of the body 12 together by snapping the projections 17 into holes 19 and projection 52 into hole 54 in the manner described above. When so assembled, it will be apparent that the trigger mechanism 20 is free to pivot about the projection 52 in a manner that will be more fully described in connection with a description of the operation of the device 10.

As best shown in FIG. 3, when the trigger mechanism 20 is in its closed position, the enlarged end 56 of the member 46 extends through the passage 38, the shoulder 55 defined by the end 56 engaging the lower surface of the barrel portion 28. When the trigger 20 is in the closed position, the member 46 is in its unflexed or rest position. To enable the end 56 to pass through the passage 38 to effect opening and closing of the trigger mechanism 20 in the manner more fully described hereinafter, it will be apparent that the member 46 must be sufficiently flexible that it may be pushed toward the rear of the body 12 until the end 56 is in alignment with the passage 38. In the preferred embodiment shown in the drawings, this is accomplished by forming the trigger mechanism 20 from a non-rigid material, e.g. polycarbonate ABS, and making the arm 47 of the member 46 sufficiently thin that it may be flexed relative to the main portion 40.

A blind transverse circular cavity 58 is provided in the handle portion 26 of the body 12 for receiving a spool of floss 24 and the cap 22. A centrally disposed axial post 62 extends from the rear defining wall 60 of the cavity 58, the post 62 being dimensioned for a clearance fit with the hole 64 in the spool of floss 24. The cap 22 is hollow, the side wall 66 of the cap being dimensioned for a friction fit with the defining walls of the cavity 58 for releasably securing the cap 22 in the body 12 for releasably retaining the spool of floss 24 in the cavity 58 during use of the device 10. Preferably, the cap 22 is formed with a lip 69 to facilitate removal of the cap 22 from the body 12 for changing the spool 24. As shown in FIG. 2, the side wall 66 of the cap 22 is provided with an axially extending slit 68, the free end of the floss from the spool 24 passing through the slit 68 and from there to the floss path defined about the body 12 and described immediately hereinafter.

The floss path about the body 12 is defined by a plurality of grooves 70, 72, 74 and 76 in the outer defining walls of the body parts 13 and 15. As shown, groove 70 is formed in the body part 15 and extends from the front of the cavity 58 to the bottom of the recess 29 at the rear end thereof. Groove 72 is also formed in the part 13 and extends from the bottom of the recess 29 at the front end thereof across the front of the prong 18. Groove 74 is formed in the body part 13 and extends from the front of the prong 16 to the bottom of the recess 29 at the front end thereof. Finally, the groove 76 is also formed in body part 13 and extends from the bottom of the recess 29 at the rear end thereof to its point of termination a short distance from the recess 29.

After the body 12 and trigger mechanism 20 have been assembled in the manner described above, the floss spool 24 is disposed on the post 62 in the cavity 58. The cap 22 is then fitted into the cavity 58, the free end 78 of the floss being held in the slit 68 in the side wall 66 of the cap as the cap is fitted in place. During this step, the user supports the cap such that the slit 68 is generally in alignment with the groove 70. If desired, alignment between slit 68 and groove 70 may be insured by providing one or more ridges on the outer surface of the cap side wall 66 and mating recesses on the defining side wall of the cavity 58. Other available techniques for insuring registration of slit 68 and groove 70 will also suggest themselves to those skilled in the art once this description is known.

With the trigger mechanism 20 in its fully opened position (phantom position FIG. 3), the floss end 78 is pulled through the groove 70, across the bottom wall 30 of the recess 29 and into the groove 74 in the other half 13 of the body 12. The floss is then pulled through the groove 74, across the space between the prongs 16, 18 and into the groove 72. From there, the floss is again pulled across the recess 29 and then into the groove 76 with the free end 78 left to dangle alongside the body 12. At this point, the trigger mechanism 20 is moved to its fully closed position (solid lines in FIG. 3) whereupon the two sections of floss which criss-cross in the recess 29 are tightly pinched between the trigger mechanism 20 and the surface 30 thereby preventing further movement of the floss in the grooves 70, 72, 74 and 76. The integrity of the securement of the floss in the recess 29 by the trigger mechanism 20 is enhanced by the ridges 48 on the trigger mechanism which seat in the complementary recesses 32 in the surface 30, the forwardmost wedge-shaped ridge 48 serving to pull the floss toward the handle as the trigger is moved to the closed position thereby aiding in the tensioning of the length of floss 80 extending between the prongs 16, 18. If desired, and as shown in FIG. 1, the surface 30 of the recess 29 and the confronting surface of the main portion 40 of the trigger 20 may be provided with dull serrations to further enhance the pinching effect.

Once the floss has been threaded about the body 12 and secured in place by closing the trigger mechanism 20 in the manner described above, the flossing device 10 is ready for use. Referring to FIG. 3, to use the device 10, the user grasps the handle portion 26 in the palm of the hand, the body 12 being shaped such that the forefinger will naturally rest on the end 56 of the trigger member 46 and the thumb will rest on the top of the trigger above the member 46. Flossing is effected by inserting the front end 14 of the barrel 28 into the mouth and then manipulating the length of floss 80 extending between the prongs 16, 18 into the space between the teeth to be cleaned. The spacing between the prongs 16 and 18 is selected at preferably about 0.625 inches whereby the length of floss 80 may be manipulated for cleaning the plaque from the sides of the teeth below the gum. It will now be apparent that the arcuate shape of the barrel portion 28 of the device 10 facilitates insertion of the device 10 into the mouth over the bottom (or top) teeth for cleaning plaque from teeth at the rear of the mouth (FIG. 3). As shown in FIG. 3, when the trigger mechanism 20 is in the closed position, the trigger 20 and barrel portion 28 present a substantially continuous, smooth surface which is both aesthetically pleasing and safe, there being no unnecessary protrusions which could injure the oral cavity during use of the device 10.

As is well known in the flossing art, after one or more teeth have been cleaned, it is desirable to use a new length of floss for the next series of cleaning operations, as the floss generally becomes soiled after cleaning one or at most a few teeth. In accordance with the present invention, to provide a new length of floss 80 between the prongs 16, 18, the user, using the forefinger, pushes back and up on the end 56 of the trigger member 46 until the mechanism 20 assumes the position illustrated in FIG. 5 wherein the end 56 is received in the passage 38. It will be apparent that in this position the trigger mechanism 20 no longer pinches the floss against the surface 30 of the recess 29, and the floss is freed for movement in the grooves 70, 72, 74 and 76. Accordingly, a new length of floss 80 may be positioned between the prongs 16, 18 by simply pulling, with the free hand, on the free end 78 of the floss extending from the groove 76. It will be apparent that as the free end 78 is pulled, the spool 24 will rotate about the post 62 and floss will be pulled through the grooves 70, 72, 74 and 76, the user pulling the floss until a new, clean length of floss 80 is disposed between the prongs 16, 18. Using the thumb, the user then pushes down on the trigger 20 until the mechanism 20 again assumes its fully closed position whereupon the device 10 is ready for the next cleaning operation. It will be apparent that the operation for advancing the floss for disposing a new length of floss 80 between the prongs 16 and 18 may be repeated as often as necessary and that this operation is easily and readily accomplished by a quite natural cooperation between the forefinger and thumb in opening and closing the trigger 20.

In the event the length of floss 80 cannot be removed in the usual fashion by vertical movement between the teeth, the user may simply move the trigger 20 to the floss advancing position (FIG. 5), whereupon the floss is freed for movement such that the free end 78 may be pulled through the side of the teeth.

Figure 6:
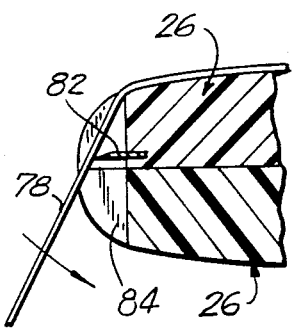
FIG. 6 is a sectional view taken substantially along the line 6—6 in FIG. 3.

Eventually the free length of floss dangling from the groove 76 will become quite long. Accordingly, and as best shown in FIG. 6, it is desirable to provide a floss cutter in the body 12, the floss cutter being shown in the rear of body 12 in the drawings. The floss cutter comprises a blade 82 disposed in a recess in the body 12 provided for that purpose. Preferably, to prevent injury to the user, the end of the blade is recessed from the outer surface of the body 12, the blade being accessible to the floss by an additional groove 84 formed in the rear of the body 12 such that the groove 84 extends across the blade 82. Accordingly, when the free end 78 of the floss becomes too long, the user simply pulls the free end into the groove 84 and across the blade 82, whereupon the blade 82 will cut the floss, the cut portion then being discarded.

When the spool of floss 24 is completely used, the user simply removes the cap 22 and discards the empty spool. A new floss spool 24 may then be inserted and threaded about the body 12 in the manner more fully described above, whereupon the device 10 is again ready for use. For commercial purposes, it may be desirable to make the cap 22 a throw away item, whereupon the cap 22 and spool 24 may be sold as a unit with the cap forming part of the packaging for protecting the spool 24 from damage. As presently contemplated, each spool 24 will have approximately seventy-five yards of floss.

It will be apparent that as the soiled floss is continuously pulled through the recess 29 as the floss is advanced, the defining walls of the recess 29 and the trigger mechanism 20 will also eventually become soiled. It is, of course, desirable to clean this area, and this is easily accomplished with the device 10 of the present invention. It will be apparent that when the trigger mechanism 20 is in the partially opened position illustrated in FIG. 5 for advancing the floss, there is insufficient clearance between the trigger 20 and the surface 30 to effect cleaning. However, by simply pivoting the trigger 20 about the projection 52 to a more fully opened position, such as that shown by the phantom lines in FIG. 3, both the trigger 20 and the recess 29 are fully exposed for cleaning. When cleaning is completed, the trigger mechanism is simply pivoted back to its fully closed position illustrated by the solid lines in FIG. 3, whereupon the device 10 is again ready for use. To facilitate movement of the member 46 through the passage 38 during opening and closing of the trigger mechanism 20, the outer surfaces of the member 46 are preferably rounded.

While we have herein shown and described the preferred embodiment of the flossing device in accordance with the present invention, those skilled in the art, upon reading this description, will appreciate that various changes and modifications may be made therein without departing from the spirit and scope of this invention. For example, while we have shown a trigger mechanism having a particular configuration, trigger mechanisms having other configurations may also be employed. Also, while the preferred floss path about the body 12 has been shown and described, other floss paths may also be devised. For example, the floss need not necessarily criss-cross across the recess 29, but rather may extend through the recess 29 in parallel fashion. Also, while a particular preferred shape for the body 12 has been illustrated and described, that shape is not absolutely essential, and other shapes may serve as well. Likewise, while a particular technique for securing the spool of floss in the body 12 has been shown and described, other techniques are available. For example, an elongate cylindrical spool of floss may be secured in the rear of the body 12 such that the axis of the spool is parallel with the axis of the body.

Since the foregoing as well as still further changes and modifications will suggest themselves to those skilled in the art once this description is known, the foregoing should be considered as illustrative only and not construed in a limiting sense, the scope of the invention being defined by the following claims.

We claim:
1. A flossing device comprising:
a body having a handle portion dimensioned for grasping by one hand of the user, and a barrel portion having a rear end extending from one end of said handle portion, the free end of said barrel portion comprising a pair of prongs defining a space therebetween;
means for securing a spool of floss to said body for rotation relative thereto;
said body defining a path for said floss from said securing means, over a surface portion of said body, across said space between said prongs, and back over said body surface portion, said body having a vertically extending bore therethrough at the rear end of said barrel portion and adjacent said surface portion;
a trigger member disposed in said bore, said trigger member including a portion defining a trigger surface, an upper part protruding through the upper end of said bore, and a lower part protruding through the lower end of said bore; and
means for securing said trigger member to said body for movement between a first position wherein said trigger surface contacts said body surface portion for securing both lengths of floss passing over said body surface portion against movement thereby tensioning the floss extending across said space between said prongs, and a second position wherein said trigger surface is spaced from said body surface portion for accommodating advancement of said floss for disposing a clean length of floss across said space by pulling on the free floss end with the other hand, said trigger member being movable between said two positions by pushing on the upper and lower parts of said trigger member, the positioning of said bore at the rear end of said barrel acommodating use of the thumb of said user's one hand for pushing on the upper part of said trigger member and the use of another finger on said user's one hand for pushing on the lower part of said trigger member, said trigger member thereby being movable between said two positions by the fingers of said user's one hand while said one hand is simultaneously holding said flossing device by grasping said handle portion.

2. The device according to claim 1, wherein said body has a plurality of grooves therein for defining said floss path.

3. The flossing device according to claim 2, wherein said grooves defining said path are discontinuous.

4. The device according to claim 1, and further comprising means operable by said user's one hand for releasably securing said trigger member in said first position.

5. The flossing device according to claim 4, wherein said means for releasably securing said trigger member in said one position comprises the free end of said second portion having an enlarged part defining a shoulder, said shoulder protruding through said bore and engaging said body when said trigger member is in said one position, said second trigger portion being moveable relative to said first trigger portion for moving said enlarged portion into alignment with said bore for moving said trigger member to said second position.

6. The flossing device according to claim 5, wherein said trigger member is integrally formed from a material sufficiently flexible to enable said second portion to be flexed relative to said first portion for moving said enlarged portion of said second portion into alignment with said bore, said enlarged portion being out of alignment with said bore with said shoulder engaging said body in the unflexed state.

7. The flossing device according to claim 6, wherein said recessed side of said barrel portion is the top surface, said trigger member being moveable from said second position to said one position by the thumb of the user's one hand, and from the one position to the second position by another of the fingers of said one hand.

8. The flossing device according to claim 7, wherein said trigger member is configured to define, with said top surface of said barrel portion, a substantially continuous surface when said trigger member is in said one position.

9. The flossing device according to claim 8, wherein said body surface portion has an indent and said trigger surface has a complementary ridge for enhancing the securement of said floss passing over said body surface portion against movement.

10. The flossing device according to claim 1, wherein said barrel portion of said body is provided with a recess, the lower defining surface of said recess comprising said body surface portion.

11. The flossing device according to claim 10, wherein said trigger securing means comprises means for pivotally securing said first portion of said trigger member to said body.

12. The flossing device according to claim 10, wherein said trigger member is configured to define, with said top surface of said barrel portion, a substantially continuous surface when said trigger member is in said one position.

13. The flossing device according to claim 1, wherein said spool securing means comprises said handle portion of said body having a cavity therein dimensioned to receive said spool, a post secured to said body and extending into said cavity, said post being dimensioned to receive a hole in the spool of floss with clearance to enable said spool of floss to rotate about said post, and cap means for covering said cavity for retaining said spool therein, and means for releasably securing said cap means to said body.

14. The flossing device ccording to claim: 13, wherein said cap means has a side wall dimensioned for a friction fit in said cavity, said friction fit comprising said cap securing means.

15. The flossing device according to claim 14, wherein said cavity is cylindrically shaped, the axis of said cavity extending transversely to said body, said cavity being opened on one side thereof, and wherein a slit for said floss is provided in said cap side wall for alignment with a groove in said body defining a section of said floss path extending from said spool securing means to said body surface portion.

16. The flossing device according to claim 1, wherein said grooves define a floss path extending from the handle portion on one side of said body, across said body surface portion to the other side of said body, along the outer surface of the prong on said other side of said body, across said space between said prongs, along the outer surface of the other prong on said one side of said body, and across said body surface portion to the other side of said body, whereby said lengths of floss overlying said body surface portion criss-cross.

17. The flossing device according to claim 1, further comprising means secured to said body for cutting the free end of said floss.

18. The flossing device according to claim 1, further comprising said trigger member being moveable to a third position wherein said trigger surface and said body surface portion are sufficiently spaced to expose said surfaces for cleaning.

19. The flossing device according to claim 18, wherein said second position and said third position comprise a single position.

20. The flossing device according to claim 18, wherein said third position comprises said trigger surface and said body surface portion being further spaced apart than in said second position.

21. The flossing device according to claim 1, wherein said barrel portion is arcuate, extending forwardly and downwardly from said handle portion.

* * * * *